United States Patent [19]

Okabe

[11] Patent Number: 5,066,800

[45] Date of Patent: Nov. 19, 1991

[54] QUNOLINE INTERMEDIATES USEFUL THEREIN FOR SYNTHESIZING ANTIBACTERIAL COMPOUNDS

[75] Inventor: Masami Okabe, Passaic, N.J.

[73] Assignee: Hoffmann-La Roche Inc., Nutley, N.J.

[21] Appl. No.: 515,958

[22] Filed: Apr. 27, 1990

[51] Int. Cl.$^5$ ............... C07D 471/06; C07D 245/00; C07D 487/06; C07D 239/28; C07D 239/00
[52] U.S. Cl. .................................... 540/471; 546/65; 546/90; 546/98; 546/99; 546/100; 546/123; 546/156; 540/476; 540/479; 540/559; 540/586; 540/576; 540/219; 540/221; 540/224; 544/247; 544/250; 544/252; 544/300; 544/310; 544/316; 544/317; 544/318; 544/319; 544/320; 544/321; 544/324; 544/327; 544/328; 544/331; 544/333; 544/361; 544/405

[58] Field of Search ................... 546/156, 123, 65, 90, 546/98, 99, 100; 544/363, 247, 250, 252, 300, 310, 316, 317, 318, 319, 320, 321, 324, 327, 328, 331, 333, 361, 405; 540/471, 476, 479, 559, 586, 576

[56] References Cited

U.S. PATENT DOCUMENTS 3,532,694 10/1970 Somerfield ..................... 546/156

*Primary Examiner*—Johann Richter
*Attorney, Agent, or Firm*—George M. Gould; Bernard S. Leon; George W. Johnston

[57] ABSTRACT

A novel process and intermediates used therein for linking a cephalosporin compound to a quinolone are disclosed. According to the disclosed process, the 2-carboxylic acid moiety of the cephalosporin compound is treated with an organic base. The resulting salt is then reacted with a quinolone compound which has been activated using a haloformate. The reaction is run in a non-aqueous organic solvent. 4-Dimethylaminopyridine is used to promote the reaction between the cephalosporin salt and the activated quinolone.

7 Claims, No Drawings

QUNOLINE INTERMEDIATES USEFUL THEREIN FOR SYNTHESIZING ANTIBACTERIAL COMPOUNDS

FIELD OF THE INVENTION

The invention concerns a novel process and intermediates used therein for linking a cephalosporin compound to a second bactericidal compound, particularly to a quinolone. Especially preferred compounds which are made according to the invention have the following formula:

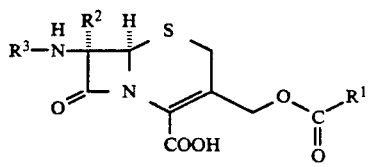

wherein $R^1$ is a quinolonyl or an azaquinolonyl group; $R^2$ is selected from the group consisting of hydrogen, lower alkoxy, amino, lower alkylthio and amido; and $R^3$ is selected from the group consisting of hydrogen and an acyl group.

Pharmaceutically acceptable salts, readily hydrolyzable esters and hydrates thereof are included within formula I.

BACKGROUND OF THE INVENTION

Processes for linking a cephalosporin, via the 3-position thereof, to a quinolone, also via the 3-position thereof, have been described in European Patent Application Publication No. 0 251 330, published July 1, 1988. The processes described therein employ a cephalosporin compound having a halomethyl substituent in the 3-position and an ester protected carboxylic acid group in the 2-position. The described processes also employ as a starting material the salt (e.g. a sodium salt) of a quinolone compound in which the salt is formed with the 3-carboxylic acid substituent of the quinolone.

The above-described cephalosporin and quinolone starting materials are then reacted to form a compound in which the cephalosporin and quinolone compounds are linked at their respective 3-positions via an ester linkage of the formula,

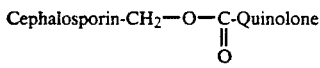

The described reaction is accompanied by a migration of the $\Delta^3$-double bond in some of the cephalosporin compounds to the $\Delta^2$-position. This results in a mixture of $\Delta^3$ and $\Delta^2$ isomers These isomers are not easily separated by chromatographic methods nor by crystallization.

Additionally, the 3-halomethyl cephalosporin compounds may decompose under the reaction conditions and the yields of the desired cephalosporin-quinolone esters are correspondingly low.

A need, therefore, exists for a process of combining a cephalosporin compound with a quinolone compound via an ester linkage where the desired $\Delta^3$-cephalosporinquinolone compound is produced in higher yields than so far have been attainable and wherein production of the unwanted $\Delta^2$-isomer is negligible. A need also exists for a process meeting the above requirements which does not require the use of chromatographic separation techniques to obtain the desired purified $\Delta^3$-isomer.

SUMMARY OF THE INVENTION

The invention provides a process, and intermediates useful therein, for making a cephalosporin-quinolone compound in which the cephalosporin and the quinolone are joined in their respective 3-positions via an ester linkage of formula

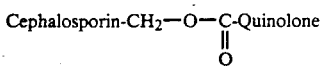

Especially preferred cephalosporin-quinolone compounds which can be made using the inventive process are those having the formula

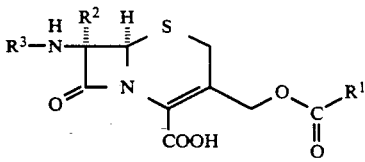

wherein $R^1$ is a quinolonyl or an azaquinolonyl group; $R^2$ is selected from the group consisting of hydrogen, lower alkoxy, amino, lower alkylthio and amido; and $R^3$ is selected from the group consisting of hydrogen and an acyl group. Pharmaceutically acceptable salts, readily hydrolyzable esters and hydrates thereof are included within formula I.

In accordance with the invention a cephalosporin of formula

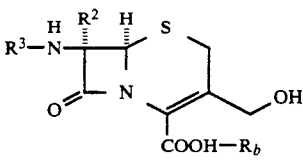

wherein $R^1$ and $R^2$ are as above; and $R_b$ is an organic base which reacts with the 2—COOH substituent to form a salt which is soluble in non-aqueous organic solvents, is reacted with an activated quinolone compound of formula

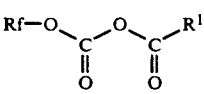

wherein $R^1$ is as defined above and $R_f$ represents alkyl, alkenyl, aryl which may be substituted, aralkyl or cycloalkyl which may be substituted.

The reaction is carried out in a non-aqueous organic solvent and in the presence of 4-dimethylaminopyridine (DMAP), or the equivalent, which is used to promote the reaction The reaction-temperature is kept lower, preferably at or below 0° C., most preferably at about −20° to −25° C.

The intermediate of formula III is made by reacting a compound of formula

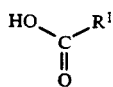

IV wherein $R^1$ is as defined above, with a haloformate of formula

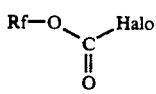

V wherein $R_f$ is as defined above and Halo represents halogen, preferably chlorine or fluorine, most preferably chlorine.

The reaction of the cephalosporin of formula II with the activated quinolone compound of formula III yields the cephalosporin-quinolone ester linked compound of formula I as well as an alcohol of formula $R_f$-OH and carbon dioxide.

Since the alcohol $R_f$-OH can compete with the cephalosporin compound (itself a primary alcohol) for reaction with unreacted quinolone, $R_f$ is preferably selected such that the alcohol $R_f$-OH is a less reactive secondary or tertiary alcohol, more preferably a secondary alcohol.

$R_f$ preferably is cycloalkyl which may be substituted or unsubstituted, alkenyl which may be substituted or unsubstituted, aralkyl, or a group of the formula

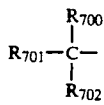

wherein $R_{700}$ and $R_{701}$ which may be the same or different are alkyl or alkenyl which may be substituted or unsubstituted more preferably $C_1$–$C_4$ lower alkyl; and $R_{702}$ is hydrogen, alkyl, or alkenyl, which may be substituted or unsubstituted, more preferably, hydrogen or $C_1$–$C_4$ lower alkyl.

Still more preferably $R_f$ represents isopropyl, isobutyl, benzyl, cyclohexyl, 2-menthyl or 2-propenyl. Most preferably, $R_f$ represents cyclohexyl.

The process according to the invention produces the desired $\Delta^3$ cephalosporin-quinolone compound in high yield, while producing the unwanted $\Delta^2$ isomer, if at all, in only negligible amount. Chromatographic techniques are not required to purify the desired $\Delta^3$ compound.

Additionally, in accordance with the invention, the activated quinolone compounds of formula III are useful as intermediates in the process described herein for reaction with a cephalosporin compound of formula II to yield a cephalosporin-quinolone ester-linked compound of formula I.

The compounds of formula I have useful antibacterial properties as will be discussed below.

DETAILED DESCRIPTION OF THE INVENTION

The invention relates to a process for making antibacterial compounds of formula

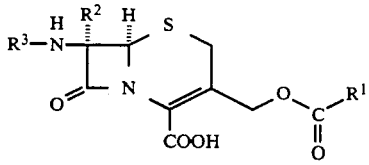

I wherein $R^1$ is a quinolonyl or an azaquinolonyl group; $R^2$ is selected from the group consisting of hydrogen, lower alkoxy, amino, lower alkylthio and amido; and $R^3$ is selected from the group consisting of hydrogen and an acyl group.

The invention also relates to intermediates which are useful in said process of formula

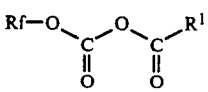

III wherein $R^1$ is as defined above and $R_f$ represents alkyl, alkenyl, aryl which may be substituted, aralkyl or cycloalkyl which may be substituted.

As used herein, and unless otherwise specified the terms "lower alkyl" and "alkyl" refer to both straight and branched chain saturated hydrocarbon groups having 1 to 8, and preferably 1 to 4, carbon atoms, for example, methyl, ethyl, propyl, isopropyl, tertiary butyl, and the like.

As used herein, the term cycloalkyl means a 3–7 membered saturated carbocyclic moiety, e.g. cyclohexyl which may be substituted with one or more alkyl or alkenyl groups.

As used herein, and unless otherwise specified the term "lower alkoxy" refers to a straight or branched chain hydrocarbonoxy group wherein the "alkyl" portion is a lower alkyl group as defined above. Examples include methoxy, ethoxy, propoxy and the like.

As used herein, the term "alkoxycarbonyl" refers to a group having the formula

—COOR$_{50}$ wherein $R_{50}$ is alkyl as defined above.

The term "halogen", or "halo", used herein refer to all four forms, that is, chloro, bromo, iodo and fluoro, unless specified otherwise.

The term "acyl" as used in conjunction with $R^3$ herein refers to all organic radicals derived from an organic acid, such as a carboxylic acid, by removal of the hydroxy group.

Although the group $R^3$ may be any one of many acyl radicals, certain acyl groups are preferred, as described below.

Exemplary acyl groups are those groups which have been used in the past to acylate beta-lactam antibiotics; particularly antibiotic derivatives of 6-aminopenicillanic acid and 7-aminocephalosporanic acid; see, for example, *Ceohalosporins and Penicillins*, edited by Flynn, Academic Press (1972), Belgian patent 866,083, published Oct. 17, 1978, Belgian patent 867,994, published Dec. 11, 1978, U.S. Pat. No. 4,152,432, issued May 1, 1979, U.S. Pat. No. 3,971,778, issued July 27, 1976, and U.S. Pat. No. 4,173,199, issued Oct. 23, 1979. The portions of these references describing various acyl groups are incorporated herein by reference. The following list of acyl groups is presented to further exemplify the term "acyl", without intending to limit that term to only those groups set forth. Exemplary acyl groups are:

(a) Aliphatic groups having the formula

wherein $R_5$ is alkyl, cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

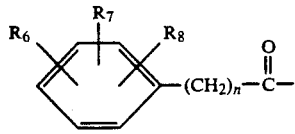

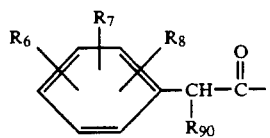

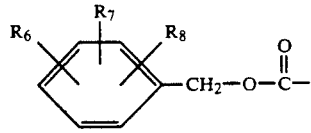

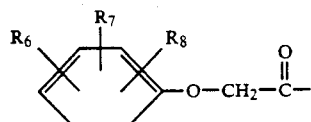

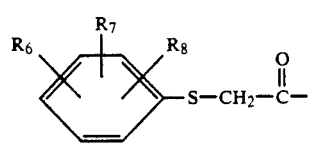

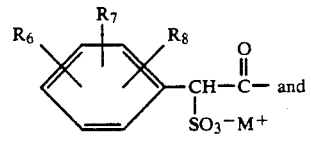

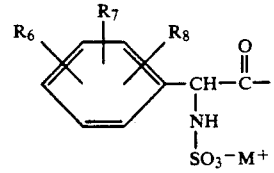

wherein n is 0, 1, 2 or 3; $R_6$, $R_7$, and $R_8$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_{90}$ is amino acylamino, hydroxy, a carboxyl salt, protected carboxy such as benzyloxycarbonyl, formyloxy or azido.

Preferred carbocyclic aromatic acyl groups include those having the formula

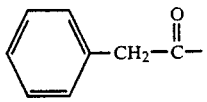

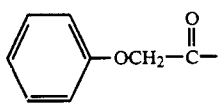

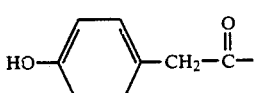

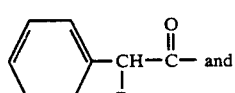

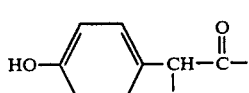

($R_{90}$ is preferably an amino group, a hydroxy group, or a carboxyl salt or sulfo salt).

Examples of other acyl groups suitable for the purposes of the present invention are sulfophenylacetyl, hydroxysulfonyloxyphenylacetyl, sufamoylphenylacetyl, (phenoxycarbonyl)phenylacetyl, (p-tolyloxycarbonyl)phenylacetyl, formyloxyphenylacetyl, carboxyphenylacetyl, formylaminophenylacetyl, benzyloxycarbonylphenylacetyl, 2-(N,N-dimethylsulfamoyl)-2-phenylacetyl, 2-bromo-2-thienylacetyl, etc.

(c) Heteroaromatic groups having the formula

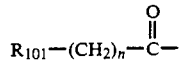

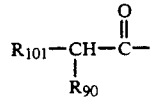

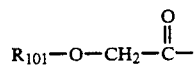

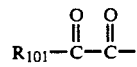

wherein n is 0, 1, 2, or 3; $R_{90}$ is as defined above; and $R_{101}$ is asubstituted or unsubstituted 5-, 6- or 7-membered heterocyclic ring containing 1, 2, 3 or 4 (preferably 1 or 2) nitrogen, oxygen or sulfur atoms. Exemplary heterocyclic rings are thienyl, furyl, pyrrolyl, pyridinyl, pyrazinyl, thiazolyl, pyrimidinyl and tetrazolyl. Exemplary substituents are halogen, hydroxy, nitro, amino, cyano, trifluoromethyl, alkyl of 1 to 4 carbon atoms, or alkoxy of 1 to 4 carbon atoms.

Preferred heteroaromatic acyl groups include those groups of the above formulas wherein $R_{101}$ is 2-amino-4-thiazolyl, 2-amino-5-halo-4-thiazolyl, 4-aminopyridin- 2-yl, 2-amino-1,3,4-thiadiazol-5-yl, 2-thienyl, 2-furanyl, 4-pyridinyl or 2,6-dichloro-4-pyridinyl.

(d) [[(4-Substituted-2,3-dioxo-1-piperazinyl)carbonyl]amino] substituted acetyl groups having the formula

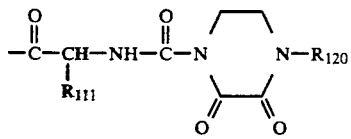

wherein $R_{111}$ is alkyl, hydroxyalkyl or an aromatic group(including carbocyclic aromatics) such as those of the formula

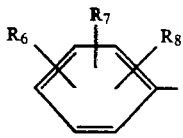

wherein $R_6$, $R_7$ and $R_8$ are as previously defined and heteroaromatics as included within the definition of $R_{101}$ and $R_{120}$ is alkyl, substituted alkyl (wherein the alkyl group is substituted with one or more halogen, cyano, nitro, amino or mercapto groups), e.g. 4-lower alkyl (preferably ethyl or methyl)-2,3-dioxo-1-piperazinecarbonyl-D-phenylglycyl.

(e) (Substituted oxyimino) arylacetyl groups having the formula

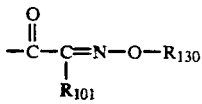

wherein $R_{101}$ is as defined above and $R_{130}$ is hydrogen, lower alkyl and $C_3$-$C_7$ cycloalkyl or substituted lower alkyl (wherein the alkyl group is substituted with 1 or more halogen, cyano, nitro, amino, mercapto, lower alkylthio, aromatic group (as defined by $R_{111}$), carboxyl (including salts thereof), amido, carbamoyl, lower alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, di-lower alkoxyphosphinyl substituents, carboxyl lower alkyl or carboxyl-$C_3$-$C_7$-cycloalkyl.

Examples of the

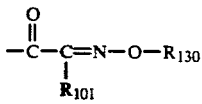

grouping are
2-[(2-chloroacetamidothiazol-4-yl)-2-[(p-nitro)benzyloxycarbonyl]methoxyimino]acetyl,
2-(2-chloroacetamidothiazol-4-yl)-2-methoxyiminoacetyl,
2-(2-aminothiazol-4-yl)-2-isopropoxyiminoacetyl),
2-(2-aminothiazol-4-yl)-2-methoxyiminoacetyl,
2-(2-aminothiazol-4-yl)-2-hydroxyiminoacetyl,
2-thienyl-2-methoxyiminoacetyl,
2-furyl-2-methoxyiminoacetyl,
2-(4-hydroxyphenyl)-2-methoxyiminoacetyl,
2-phenyl-2-methoxyiminoacetyl,
2-phenyl-2-hydroxyiminoacetyl,
2-thienyl-2-hydroxyiminoacetyl,
2-thienyl-2-(dichloroacetyloxyimino)acetyl,
2-[4-(gamma-D-glutamyloxy)phenyl]-2-hydroxyiminoacetyl,
2-[4-(3-amino-3-carboxypropoxy)phenyl]-2-hydroxyiminoacetyl,
2-(5-chloro-2-chloroacetamidothiazol-4-yl)-2-methoxyiminoacetyl,
2-(5-chloro-2-aminothiazol-4-yl)-2-methoxyiminoacetyl,
2-[2-(t-butoxycarbonyl)isopropoxyimino]-2-(2-sulfoaminothiazol-4-yl)acetyl,
2-[2-(t-butoxycarbonyl)isopropoxyimino]-2-(2-triphenylmethylaminothiazol-4-yl)acetyl,
2-(2-chloroacetamidothiazol-4-yl)-2-(isopropoxyimino)acetyl,
2-methoxyimino-2-(2-sulfoaminothiazol-4-yl)acetyl,
2-[(2-aminothiazol-4-yl)-2-carboxymethoxyimino]acetyl,
2-[(2-mesylaminothiazol)-4-yl]-2-isopropoxyiminoacetyl,
2-(2-imino-3-mesyl-4-thiazolin-4-yl)-2-isopropoxyiminoacetyl,
2-(2-aminothiazol-4-yl)-2-(carboxyisopropoxyimino)acetyl, etc.

A particularly preferred acyl group has the formula:

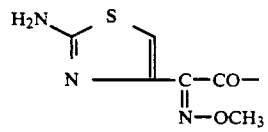

(f) (Acylamino) substituted acetyl groups having the formula

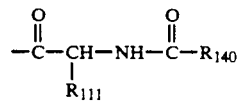

wherein $R_{111}$ is as defined above and $R_{140}$ is

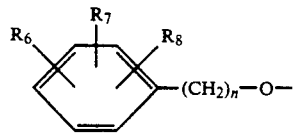

(where $R_6$, $R_7$, $R_8$ and n are as previously defined), hydrogen. lower alkyl, substituted lower alkyl, amino, alkylamino, dialkylamino, (cyanoalkyl)amino, or acylamino.

Preferred (acylamino)arylacetyl groups of the above formula include those groups wherein $R_{140}$ is amino, or acylamino. Also preferred are those groups wherein $R_{111}$ is phenyl or 2-thienyl.

(g) (Substituted oxyimino) substituted acetyl groups having the formula

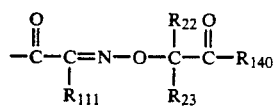

wherein R$_{111}$ and R$_{140}$ are as defined above, and R$_{22}$ and R$_{23}$ are independently selected from the group consisting of hydrogen and lower alkyl, or R$_{22}$ and R$_{23}$ taken together with the carbon atom to which they are attached form a C$_3$–C$_7$ carbocyclic ring, for example, cyclopropyl, cyclobutyl or cyclopentyl.

Preferred (substituted oxyimino) substituted acetyl groups of the above formula include those groups wherein R$_{140}$ is amino. Also preferred are those groups wherein R$_{111}$ is 4-thiazolyl.

(h) [[[3-Substituted-2-oxo-1-imidazolidinyl] carbonyl]amino] substituted acetyl groups having the formula

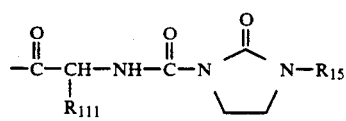

wherein R$_{111}$ is as defined above and R$_{15}$ is hydrogen, alkylsulfonyl, arylmethyleneamino (i.e., —N=CHR$_{111}$ wherein R$_{111}$ is as defined above),

(wherein R$_{16}$ is hydrogen, alkyl or halogen substituted alkyl), aromatic group (as defined by R$_{111}$ above), alkyl or substituted alkyl (wherein the alkyl group is substituted with one or more halogen, cyano, nitro, amino or mercapto groups).

Preferred [[[3-substituted-2-oxo-1-imidazolidinyl]-carbonyl]-amino]arylacetylgroups of the above formula include those wherein R$_{111}$ is phenyl or 2-thienyl. Also preferred are those groups wherein R$_{15}$ is hydrogen, methylsulfonyl, phenylmethylenamino or 2-furylmethylenamino.

A skilled artisan would recognize that suitable acyl groups include those acyl moieties found on: cefaclor, cefadroxil, cefamandole, cefazedone, cefazolin, cefbuperazone, cefixime, cefmetazole, cefminox, ceforanide, cefortetan, cefoteam, cefoxitim, cefpimizole, cefpiramide, cefroxadine, cefsulodin, ceftazidime, ceftibuten and cefuroxime.

As used herein the quinolonyl or azaquinolonyl substituent R$^1$ include, among others, substituents of the formulas

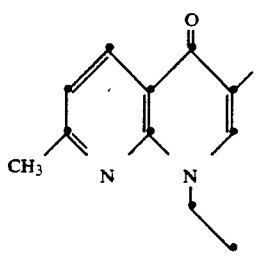

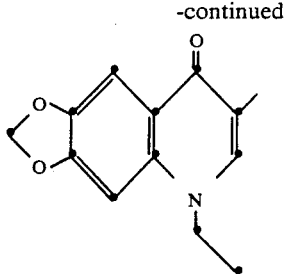

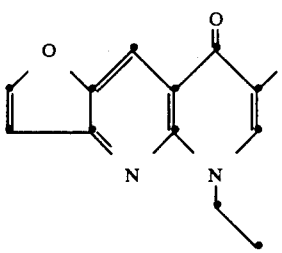

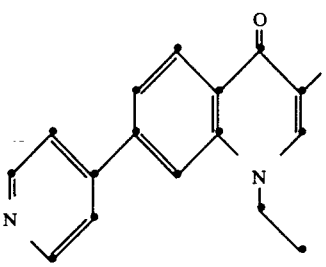

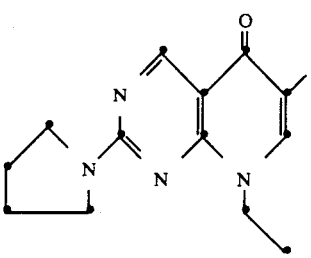

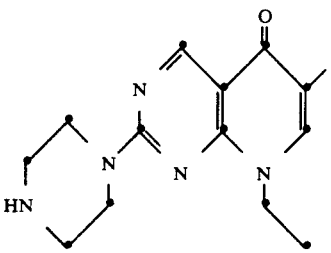

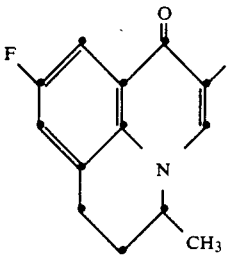

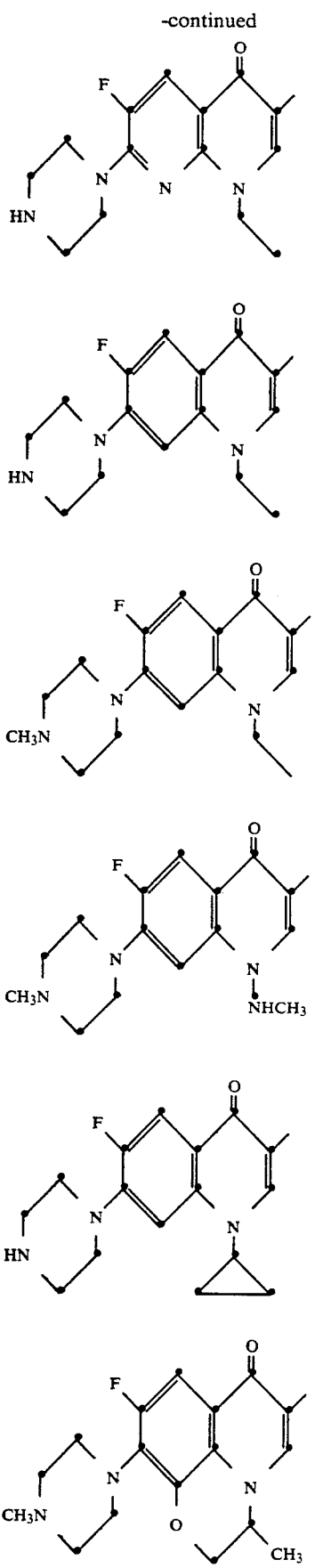
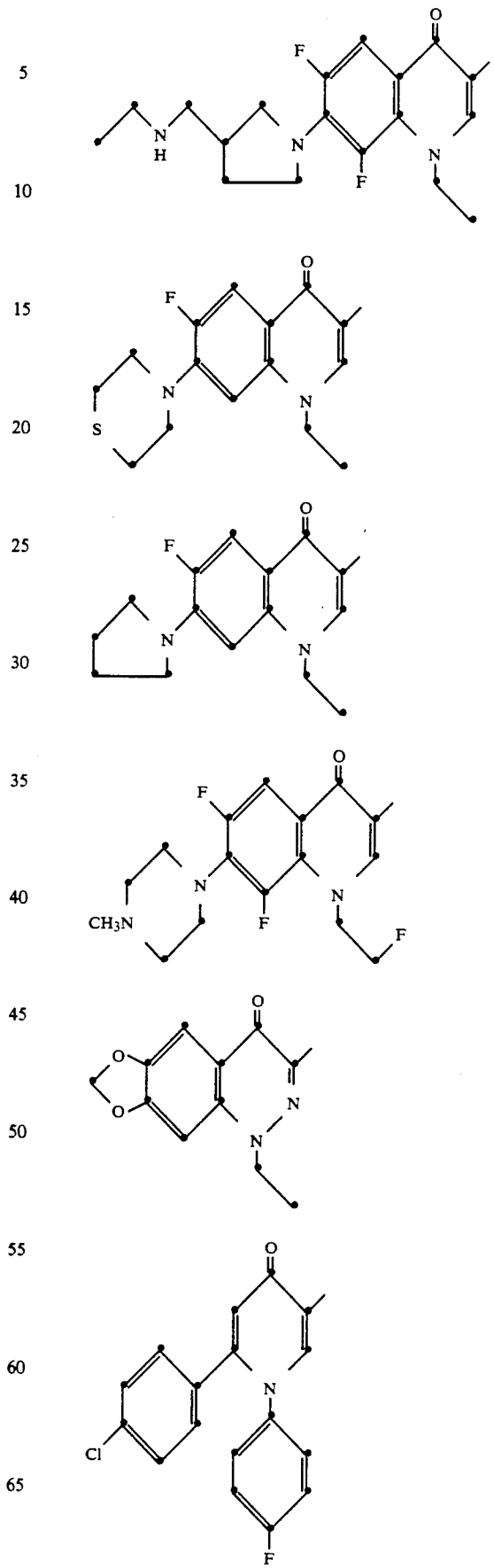

-continued

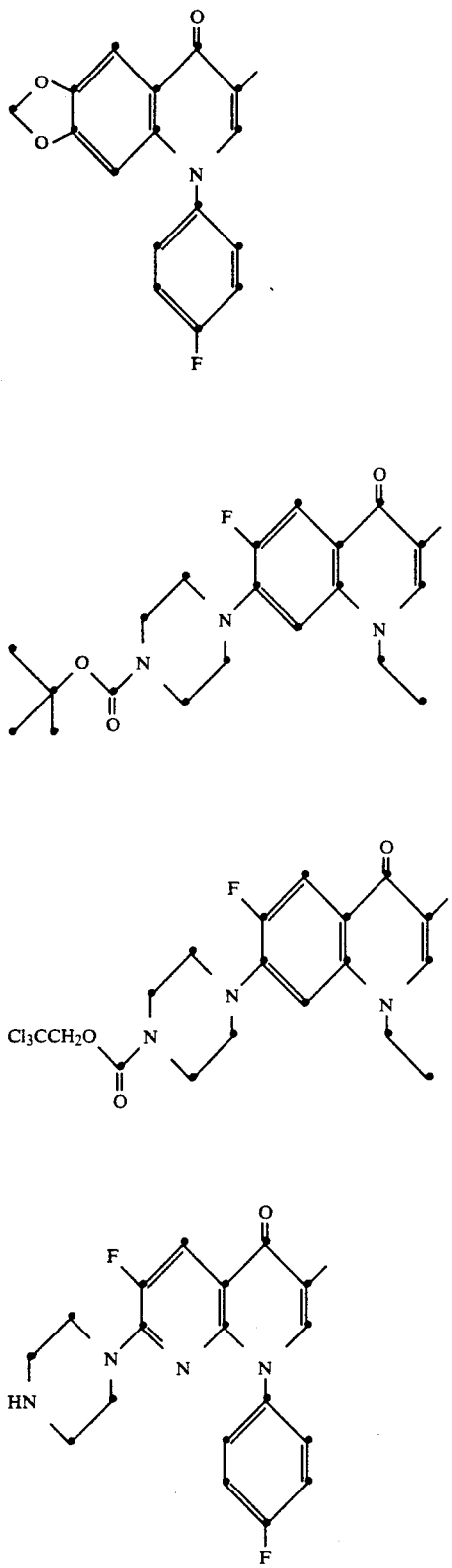

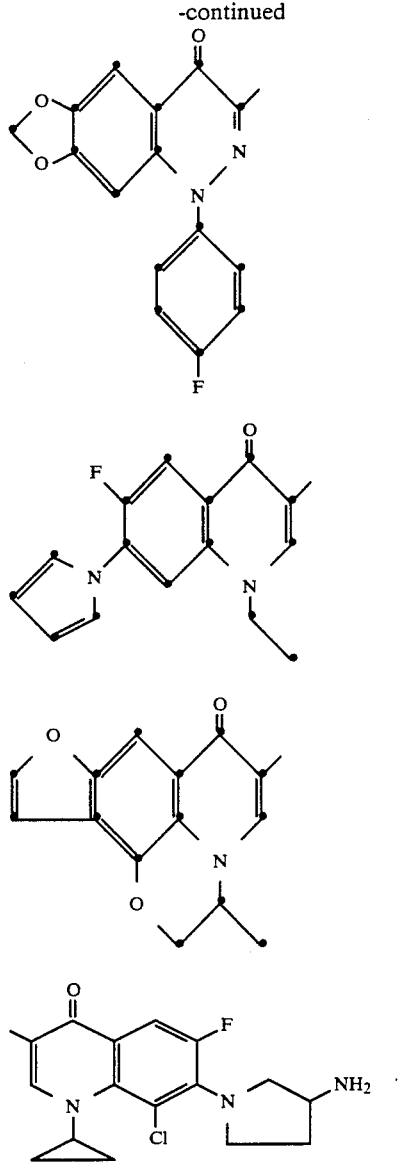

By the terms "aryl" and "carbocyclic aryl" are meant an aromatic moiety, such as, phenyl, tolyl, xylyl, mesityl, cumenyl, naphthyl, and the like, which may be substituted with 1 to 3 suitable substituents, such as halo (fluoro, chloro, bromo, etc.), hydroxy, lower alkyl, amino, cyano, lower alkoxy, alkoxycarbonyl, and the like.

By the term "alkyl carbocyclic aryl" is meant a group of formula

wherein n=1, 2 or 3 and $R_{51}$ is a carbocyclic aryl as defined above.

By the term "lower alkanoyl" or "alkanoyl" as utilized herein is intended a moiety of the formula

wherein $R_{25}$ is H or $C_1$ to $C_6$ lower alkanoic acid, e.g., acetyl, formyl, propionyl, butyryl and the like.

By the term "substituted phenyl" is meant phenyl mono-or di-substituted by halo(chloro, bromo, fluoro, etc.), lower alkyl, lower alkenyl, amino, nitro or trifluoromethyl.

By the term "substituted alkyl" is meant a "lower alkyl" moiety substituted by, for example, halo (chloro, fluoro, bromo, etc.), trifluoromethyl, amino, cyano, etc.

By the terms "alkenyl" and "lower alkenyl" are meant straight or branched chain hydrocarbon groups which contain an olefinic double bond having 2 to 6 carbon atoms, i.e., the radical of compounds of the formula $C_nH_{2n}$ wherein n is 2 to 6, e.g. propenyl, vinyl, etc.

By the term "aralkyl" is meant a hydrocarbon group having both aromatic and aliphatic structures, that is, a hydrocarbon group in which a lower alkyl hydrogen atom is substituted by a monocylic aryl group, e.g., phenyl, tolyl, etc.

The expression "5- or 6- membered heterocyclic ring containing 1–4 hetero atoms selected from the group consisting of O, N and S" is intended to represent the following groups: pyridyl, piperidyl, piperidino, N-oxido-pyridyl, pyrimidyl, piperazinyl, pyrolidinyl, pyridazinyl, N-oxide-pyridazinyl, etc. a 5-membered nitrogen-containing hetero ring, e.g., pyrazolyl, imidazolyl, thiazolyl. 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, lH-tetrazolyl, 2H-tetrazolyl, etc., and others. Each of these hetero rings may be further substituted and, as the substituents, there may be mentioned, for example, lower alkyls such as methyl, ethyl, propyl, etc., lower alkoxys such as methoxy, ethoxy, etc., halogens such as chlorine, bromine, etc., halogen substituted alkyls such as trifluoromethyl, trichloroethyl, etc., aminoethyl, ethylaminomethyl, amino, mercapto, hydroxy, carbamoyl, carboxyl group, etc.

By the term "cycloalkenyl" is meant a 3–8 membered unsaturated carbocyclic moiety, e.g. cyclobutenyl, cyclohexenyl, etc., which may be substituted with one or more alkyl or alkenyl groups.

As readily hydrolyzable esters of the compounds of formula I there are to be understood compounds of formula I, the carboxy group(s) of which (i.e., the 2-carboxy group) is/are present in the form of readily hydrolyzable ester groups. Examples of such esters, which can be of the conventional type, are the lower alkanoyloxyalkyl esters (e.g., the acetoxymethyl, pivaloyloxymethyl, 1-acetoxyethyl and 1-pivaloyloxyethyl ester), the lower alkoxycarbonyloxyalkyl esters (e.g., the methoxycarbonyloxymethyl, 1-ethoxycarbonyloxyethyl and 1-isopropoxycarbonyloxyethyl ester), the lactonyl esters (e.g., the phthalidyl and thiophthalidyl ester), the lower alkoxymethyl esters (e.g., the methoxymethyl ester) and the lower alkanoylaminomethyl esters (e.g., the acetamidomethyl ester). Other esters (e.g., the benzyl and cyanomethyl esters) can also be used.

It is to be understood that in accordance with the invention, when reacting the cephalosporin compound of formula II with the activated quinolone of formula III, the 2-carboxylic acid moiety of the cephalosporin should not be protected with conventional protecting groups—e.g., esters. Rather, prior to reaction, the carboxylic acid group in the 2-position of the cephalosporin compound of formula II is preferably reacted with an organic base (preferably, a tertiary amine or quaternary ammonium hydroxide—most preferably, tributylamine) which forms an ionic bond therewith. Additionally, as some inorganic salts would not be soluble in nonaqueous organic solvents, such inorganic salts of the compound of formula II are not contemplated as being useful in carrying out the process according to the invention.

Following the reaction of the cephalosporin compound of formula II with the activated quinolone of formula III, the organic base employed may be removed. If desired the obtained product may then be converted into any of a number of pharmaceutically acceptable salts. Examples of such pharmaceutically acceptable salts of the compounds of formula I are alkali metal salts such as the sodium and potassium salt, the ammonium salt, alkaline earth metal salts such as the calcium salt, salts with organic bases such as salts with amines (e.g., salts with N-ethyl-piperidine, procaine, dibenzylamine, N,N'-dibenzylethylenediamine, alkylamines or dialkylamines) as well as salts with amino acids such as, for example, salts with arginine or lysine.

The compounds of formula I when they contain a basic functional group such as an amine, also form addition salts with organic or inorganic acids. Examples of such salts are hydrohalides (e.g. hydrochlorides, hydrobromides and hydroiodides) as well as other mineral and acid salts such as sulphates, nitrates, phosphates and the like, alkylsulphonates and monoarylsulphonates such as ethanesulphonates, toluensulphonates, benzenesulphonates and the like, and also other organic acid salts such as acetates, tartrates, maleates, citrates, benzoates, salicylates, ascorbates and the like.

The compounds of formula I as well as their salts and readily hydrolyzable esters can be hydrates. The hydration can be effected in the course of the manufacturing process or can occur gradually as a result of hygroscopic properties of an initially anhydrous product.

A preferred class of compounds which can be made using the processes according to the invention are of the formula

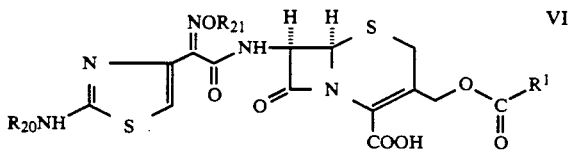

wherein $R^1$ is as above $R_{20}$ is hydrogen or an amino protecting group, for example, trityl or chloroacetyl, and $R_{21}$ is hydrogen, lower alkyl or a group of the formula

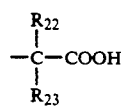

wherein $R_{22}$ and $R_{23}$ are as defined above.

Specifically preferred are compounds of the formula

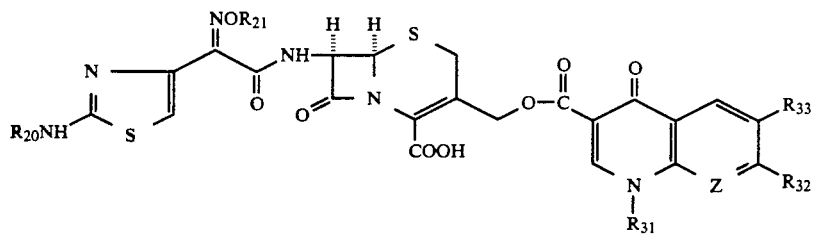

VIA wherein $R^1$, halo and $R_f$ are as defined above.

Scheme I

V + IV → III

A haloformate of formula V, which is known or made by analogy (See, Matzner, M., et al., Chemical Reviews, Vol. 64, pp. 645-656 (1964) is reacted with a quinolone of formula IV to yield the desired activated quinolone of formula III.

The reaction is carried out in a non-aqueous organic solvent, e.g, methylene chloride. Preferably, an organic base, e.g. tributylamine or the equivalent is employed to take up the acid which is produced during the reaction.

The reaction temperature is preferably maintained at about 0° C. However persons skilled in the art will be able to adjust the reaction temperature up or down depending upon the particular reactants employed.

If desired compound III can be purified and/or isolated by employing conventional techniques.

Scheme II—Preparation of Cephalosporin Intermediate

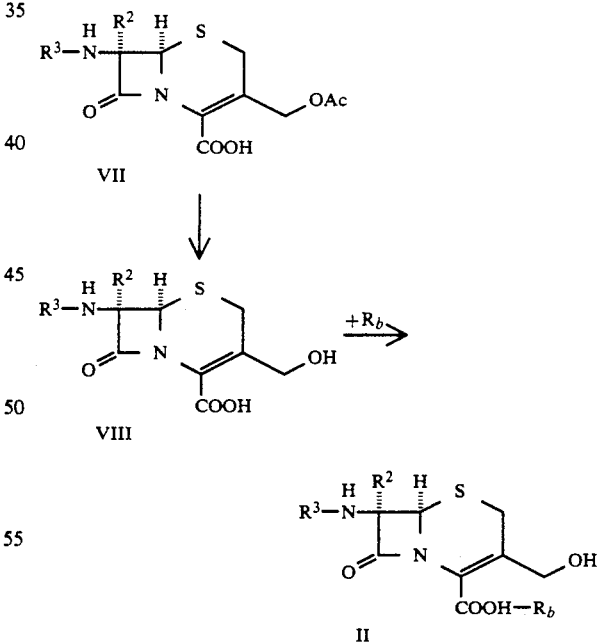

wherein $R^2$ $R^3$ and $R_b$ are as defined above.

Scheme II

VII → VIII

A compound of formula VII, which is known or made by analogy, (see, e.g., Takaya et al, J. Antibiotics, Vol. 34, pp 1300-1310 (1981), U.S. Pat. No. 3,445,463, and European Patent Application No. 0 265 185) is wherein $R_{20}$, $R_{21}$, are as above and Z represents

or N, $R_{30}$ represents hydrogen or halogen; $R_{31}$ hydrogen, lower alkyl, lower alkenyl, $C_3$-$C_7$ cycloalkyl, halo lower alkyl or mono, di and tri-halophenyl; $R_{30}$ and $R_{31}$ when taken together represents lower alkylene of 3-5 carbon atoms, a lower alkylene mono-oxy group of 2-4 carbon atoms or a lower alkylene dioxy group having 1-2 carbon atoms.

Compounds of the formula I, their salts and esters and hydrates of those compounds can be used as agents to combat bacterial infections (including urinary tract infections and respiratory infections) in a mammalian species, e.g., dogs, cats, horses, etc., and humans. The cephalosporins exhibit activity against a broad range of both gram-negative and gram-positive bacteria.

All modes of administration which have been used in the past to deliver penicillins and cephalosporins to the site of the infection are also contemplated for use with the dual action cephalosporins produced by this invention. Such methods of administration include intravenous, intramuscular and enterally, e.g., as a suppository.

The following reaction schemes set forth the methods and intermediates useful in producing the novel end products of formula I.

In the following reaction sequences where a substituent group is present which may be attacked during the reaction it should be in protected form utilizing well known protecting groups. For example amino groups may be protected with easily removable protective groups employed in peptide chemistry, such as an alkoxycarbonyl group, e.g., t-butoxycarbonyl, etc., a substituted alkoxycarbonyl group, e.g. trichloroethoxycarbonyl, etc., a substituted alkylcarbonyl, e.g., monochloromethylcarbonyl, or a substituted aralkyloxycarbonyl group, e.g., p-nitrobenzyloxycarbonyl.

A preferred protecting group is t-butoxycarbonyl (t-BOC).

Scheme I—Preparation of Activated Quinolone Intermediate

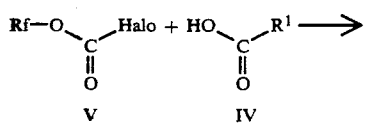

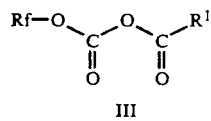

hydrolyzed in known manner to produce the 3-hydroxymethyl cephalosporin compound of formula VIII.

VIII→II

Compound VIII is reacted with an organic base $R_b$ in a non-aqueous organic solvent, e.g. methylene chloride to form a salt of formula II. The reaction can be carried out at room temperature.

The organic base is preferably a tertiary amine, of the formula

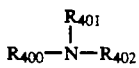

wherein $R_{400}$, $R_{401}$ and $R_{402}$, which may be the same or different, are alkyl, preferably $C_1$-$C_4$ lower alkyl, most preferably tributylamine.

Scheme III—Combination of Cephalosporin With Activated Quinolone

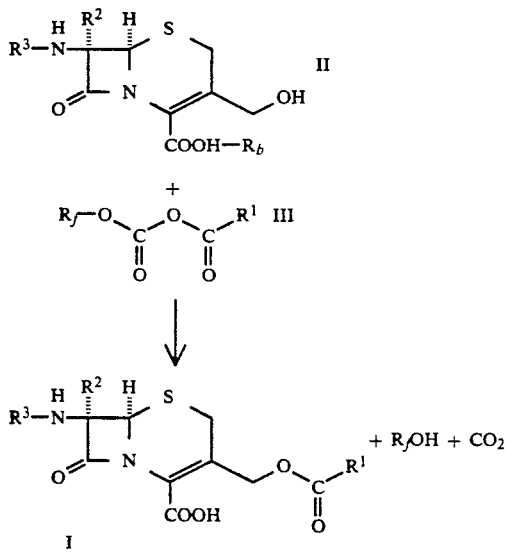

wherein $R^1$, $R^2$, $R^3$, $R_b$ and $R_f$ are as defined above.

Scheme III

II+III→I

The activated quinolone of formula III is dissolved in a non-aqueous organic solvent, e.g. methylene chloride, and the solution is cooled preferably to about $-25°$ C. If desired, the activated quinolone of formula III can be prepared in situ by following Scheme I, without undergoing purification. The cephalosporin of formula II is then added along with an agent, such as 4-dimethylaminopyridine (DMAP), or the equivalent, which helps promote the reaction of compounds II and III. The reaction mixture is maintained at a temperature of about $-20°$ to $-25°$ C. for about 2 hours and then slowly warmed to about $0°$ C. over a period of about 1.5 hours. Compound I is then purified employing conventional techniques.

The inventive process overcomes several problems encountered in synthesizing the compounds of formula I, including:

1) $\Delta^3$ to $\Delta^2$ bond migration in the cephalosporin compound;

2) lactone formation wherein the 2-carboxylic acid group of the cephalosporin reacts with the 3-hydroxy methyl group to form a lactone ring;

3) unwanted reaction of the quinolone with the 2-carboxylic acid group rather than with the 3-hydroxy methyl group of the cephalosporin compound, which also results in lactone formation;

4) preferential formation of the unwanted lactone over formation of the desired cephalosporin-quinolone ester linked compound; and 5) the need for chromatographic techniques to purify the compound of formula I.

Thus, one important aspect of the invention is that the cephalosporin compound of formula II is a salt formed by reaction of an organic base with the 2-carboxylic acid substituent. It is conventional to protect the 2-carboxylic acid group by forming an ester therewith. However, this has the drawback of promoting $\Delta^3$ to $\Delta^2$ bond migration. Since a conventional protection of the 2-carboxylic acid of the cephalosporin of formula II as an ester promotes $\Delta^3$ to $\Delta^2$ isomerization during acylation of the 3-hydroxymethyl group, the 2-carboxylic acid, in accordance with the invention is left unprotected. On the other hand, the 2-carboxylic acid group is Prone to react with the 3-hydroxymethyl group to form a lactone, thus, in accordance with the invention, an organic base is used in order to suppress such reaction. When the organic base is triethylamine, lactonization may occur slowly under a high vacuum or at a higher temperature (such as $45°$ C.) over a period of several hours. However, when the organic base is tributylamine no lactonization occurred under the same conditions over the same time period. Therefore, depending on the conditions used for drying the cephalosporin of formula II prior to its use in the reaction with the activated quinolone compound of formula III, persons skilled in the art will be able to choose as the organic base, a compound which yields the desired degree of resistance to lactonization.

Another aspect of the invention involves the selection of the activating agent which is used to make the activated, quinolone of formula III. As noted in Table II above, the selection of the activating agent affects overall yield of the desired ester of formula I as well as the ratio of the desired ester to the undesired lactone. The chloroformates as a group performed better than the other activating groups that were tried. Thus, trimethylacetoxy afforded an unfavorable ester to lactone ratio of 1:2 and a poor yield of only about 10% based on NMR analysis of the crude product.

Fluoride, which was prepared in situ by using 1-methyl-2-fluoropyridinium p-toluenesulfonate, afforded only 19% yield of the desired ester, although an ester to lactone ratio of 4:1 was obtained.

When no activating agent was used (i.e. X=OH), no reaction occurred.

The selection of the haloformate of formula V to make the activated quinolone of formula III is also important. Alkyl chloroformates, such as isobutyl chloroformate or cyclohexyl chloroformate and aralkyl chloroformates, such as benzyl chloroformate, gave nearly identical ratios of ester to lactone (4:1). However, alkenyl chloroformates, such as propenyl chloroformate, gave a lower ester to lactone ratio of 2:1.

It is preferable that the alcohol $R_fOH$, which is formed during the reaction of the activated quinolone of formula III with the cephalosporin of formula II, be less reactive than the cephalosporin. Therefore, $R_f$ is preferably chosen so that a higher overall yield of the desired ester of formula I would be obtained. Secondary alkyl chloroformates, which produce secondary alcohols (the cephalosporin being a more reactive primary alcohol), such as cyclohexyl chloroformate and 2-menthyl chloroformate, gave better yields over the chloroformates which produce primary alcohols, such as isobutyl chloroformate or benzylchloroformate. Cyclohexyl chloroformate gave the best result in overall yield (56%).

The invention will now be exemplified with reference to the synthesis of especially preferred end products.

EXAMPLE 1

Step 1

Preparation of crude
[6R-[6alpha,7beta(Z)]]-3-[(Acetoyloxy)methyl]-7-[[(methoxyimino)[2-[triphenylmethyl)amino]-4-thiazolyl]acetyl]amino-8-oxo-5-thia-1-azabicyclo [4,2,0]oct-2-ene-2carboxylic acid (1:1)triethylamine salt A 500-mL three-necked flask equipped with a mechanical stirrer and an Ar bubbler was charged with 33.5 g (0.12 mol) of triphenylmethyl chloride, 35.05 g (0.10 mol) of 2-mercaptobenzthiazoyl-2-(2-aminothiazoyl-4-yl)-2-methoxyamino acetate (MAEM), 100 mL of $CH_2Cl_2$, and 18.1 mL of triethylamine (0.13 mol), slightly exothermic. This suspension was stirred at room temperature overnight and then the resulting red solution was cooled with an ice-water bath. To this mixture, 18.1 mL of triethylamine (0.13 mol), 27.2 g of 7-ACA (0.10 mol), and 50 mL of $CH_2Cl_2$ was added. This mixture was stirred at that temperature for 10 minutes and then at room temperature for 1.5 hrs, and then transferred to a round-bottomed flask. The solvent was removed by evaporation at 25° C./70 mmHg and the resulting solid was further dried overnight at room temperature/0.2 mmHg to afford 130 g of the named compound.

Step 2

Preparation of crude [6R-[6alpha,7beta(Z)]]-3-(Hydroxymethyl)-7-[(methoxyimino)[2-[(triphenylmethyl)amino]-4-thiazolyl]acetyl]amino]-8-oxo-5-thia-1-azabicyclo[4.2.0]oct-2-ene-carboxylic acid (1:1)tributylamine salt A 2-L three-necked flask equipped with a thermometer, an Ar bubbler, and an addition funnel was charged with 130 g of crude [6R-[6alpha,7beta(Z)]]-3-[(Acetyloxy)methyl]7-[[(methoxyimino)[2-[(triphenylmethyl)amino]-4-thiazolyl]acetyl]amino]-8-oxo-5-thia-1-azabicyclo[4.2.0]oct-2-ene-2carboxylic acid (1:1) triethylamine salt and 600 mL of methanol. After cooling to −30° C., 300 mL of 1.5N NaOH (0.45 mol) was added dropwise over one hour to the red solution, while the temperature was maintained between −20° to −25° C. The reaction mixture was stirred at the temperature for an additional hour To this mixture, 200 mL of 3N HCl was added dropwise at −10° to −20° C. followed by 600 mL of ice-cold $CH_2Cl_2$. The mixture was stirred until all solids dissolved. The cold organic layer was separated and washed with 200 mL of 50% aq. methanol. The organic layer was separated and 30 mL of tributylamine was added. After warming to room temperature, this solution was washed with 100 mL of 30% aq. methanol and dried over $Na_2SO_4$. The drying agent was removed by filtration and washed with $CH_2Cl_2$. The combined filtrate and washings were concentrated by evaporation at room temperature/70 mmHg. The resulting foam was dried overnight at room temperature/0.2 mmHg.

This foam was resuspended in 400 mL of ether, stirred at room temperature for 4 hr, then filtered and washed with 3×100 mL (i.e. 300 mL) of ether. The solid was further dried for 24 hr at room temperature/0.2 mmHg to afford 89.7 g of the named compound.

Step 3

Preparation of 6R-[6alpha,7beta(Z)]1-3-[[6,8-Difluoro-1-(2-fluoroethyl)-1,4-dihydro-7-(4-methyl-1-piperazinyl)-4-oxo-3-quinolinyl]carbonyl]oxy]methyl]-7-[[(methoxyimino)[2-[(triphenylmethyl)amino]-4-thiazolyl]-acetyl]amino]-8-oxo-5-thia-1-azabicyclo[4.2.-0]oct-2-ene-2carboxylic acid In a 2-L three-necked flask equipped with a mechanical stirrer a thermometer, and an Ar bubbler, 36.9 g of fleroxacin (0.10 mol) was suspended in 700 mL of $CH_2Cl_2$ (dried over molecular sieves) After this suspension was cooled to 0° C., 15.2 mL of cyclohexyl chloroformate (0.105 mol) was added followed by 26 mL of tributylamine (0.11 mol)(dried over KOH). After the resulting yellow solution was cooled to −25° C., 89.7 g of crude alcohol [6R-[6alpha, 7beta(Z)]]-3-(Hydroxymethyl)-7-[[(methoxyimino)[2-[(triphenylmethyl)amino]-4-thiazolyl]acetyl]amino]-8-oxo-5-thia-1-azabicyclo[4.2.0]oct-2-ene-2-carboxylic acid (1:1) tributylamine salt was added with the aid of 50 mL of $CH_2Cl_2$. After dissolution of the alcohol, 3.05 g of 4-dimethylaminopyridine (25 mmol) was added, and the reaction mixture was stirred at −20° to −25° C. for 2 hr and then slowly warmed to 0° C. over 1.5 hr. To this, 500 mL of acetone was added and the mixture was stirred for 20 min. The precipitate was filtered, washed with a total of 250 mL of acetone, and dried at 0.2 mmHg overnight to recover 7.98 g of unreacted fleroxacin (21.6%). To the combined filtrate and washings, 2 L of hexane was added to precipitate the product, which was filtered, washed with 300 mL of acetone-hexane (2:1) and then with 150 mL of hexane, and dried overnight at room temperature/0.2 mmHg. This crude product was added to 500 mL of $CH_2Cl_2$. To the resulting dark solution, 1.5 L of acetone was added dropwise and the precipitate was filtered and washed with 2×150 mL (i.e., 300 mL) of acetone and then with 2×150 mL (i.e., 300 mL) of ether. After drying at room temperature/0.2 mmHg for 24 hr, 56.8 g of the named product (56% yield based on 7-ACA), contaminated with small amounts of fleroxacin and 4-dimethylaminopyridine, was obtained.

Step 4

Preparation of
[6R-[6alpha,7beta(Z)]]-7-[[(2-Amino-4-thiazolyl)(methoxyimino)acetyl]amino]-3-[[[[6,8-difluoro-b 1-(2-fluoroethyl)-1,4-dihydro-7-(4-methyl-1-piperazinyl)-4-oxo-3-quinolinyl]carbonyl]oxy] methyl]-8-oxo-5-thia-1-azabicyclo-[4,2,0]oct-2-ene-2-carboxylicacid bis-trifluoroacetate salt A 1-L three-necked flask equipped with a mechanical stirrer, a thermometer, and an Ar bubbler was charged with 114 mL of trifluoroacetic acid and 50 mL of $CH_2Cl_2$. After the mixture was cooled to −10° C., 56.8 g of [6R-[6alpha,7beta(Z)]]-3-[[[[6,8-Difluoro-1-(2- fluoroethyl)-1, 4-dihydro-7-(4-methyl-1-piperazinyl)-4-oxo-3-quinolinyl]carbonyl]oxy]methyl]-7-[[(methoxyimino)[2-[(triphenylmethyl) amino]-4-thiazolyl]acetyl]amino]-8-oxo-5-thia-1-azabicyclo [4.2.0]oct-2-ene-2-carboxylic acid (56 mmol) was added in portions. The walls were washed with a total of 64 mL CH$_2$Cl$_2$. The mixture was stirred at 0° C. for 3 hr. The stirring was stopped and 228 mL of hexane followed by 460 mL of ether was added gently as not to disturb the lower TFA layer. The two layers were mixed by vigorous stirring causing the precipitation of a powder. The solid was filtered, washed with a total of 800 mL of ether, and air-dried for 30 min to obtain the named product. A 1L flask equipped with a mechanical stirrer and a thermometer was charged with 300 mL of CH$_2$Cl$_2$ and 40 mL of ether. After the mixture was cooled with an ice-water bath, the [6R-[6alpha,7beta(Z)]]-7-[[(2-Amino-4-thiazolyl)( methoxyimino) acetyl]amino]-3-[[[[6,8-difluoro-1-(2-fluoroethyl)-1,4-dihydro -7-(4-methyl-1-piperazinyl)-4-oxo-3-quinolinyl]carbonyl]oxy]methyl]-8-oxo-5-thia-1-azabicyclo[4.2.0]oct-2,-ene-2-carboxylic acid bis-trifluoroacetate salt obtained above was added portionwise with the aid of 100 mL of CH$_2$Cl$_2$. The suspension was stirred at that temperature for 3 hr. Then the solid was filtered and washed with 2×100 mL (i.e. 200 ml) of CH$_2$Cl$_2$ and then with a total of 400 mL of ether. The solid was dried overnight at room temperature/0.2 mmHg to afford 51.9 g of the named compound (52% overall yield based on 7-ACA)(86% purity on HPLC).

Step 5

Preparation of
[6R-[6alpha,7beta(Z)]]-7-[[(2-Amino-4-thiazolyl)(methoxyimino)acetyl]amino]-3-[[[[6,8-difluoro-1-(2-fluoroethyl)-1,4-dihydro-7-(4-methyl-1-piperazinyl)-4-oxo-3-quinolinyl]carbonyl]oxy]methyl]-8-oxo-5-thia-1-azabicyclo 4.2.0]oct-2-ene-2-carboxylic acid dihydrochloride salt A 5 liter three-neck, round-bottom flask, equipped with a mechanical stirrer, a thermometer and a nitrogen gas inlet was charged with 927.5 mL of acetone and 271 mL of pyrogen-free water. The mixture was stirred vigorously and cooled to 0°-2° C. in an ice water bath. 250 g of [6R-[6alpha,7beta(Z)]]-7-[[(2-Amino-4-thiazolyl)(methoxyimino) acetyl]amino]-3-[[[[6,8-difluoro-1-(2-fluoroethyl)-1,4-dihydro -7-(4-methyl-1-piperazinyl)-4-oxo-3-quinolinyl]carbonyl]oxy]methyl]-8-oxo-5-thia-1-azabicyclo[4.2.0]oct-2-ene-2-carboxylic acid bis-trifluoroacetate salt was added slowly and stirring was continued for 15 minutes. The mixture was filtered through a medium-frit glass filter directly into a 12 liter three-neck, round-bottom flask equipped with a mechanical stirrer, a thermometer and a nitrogen gas inlet and the filter was washed with 50 mL of 1:1 acetone:water. To the stirred, combined filtrates was then added, at a fast dropwise rate, 657 mL of 1.0N aqueous hydrochloric acid solution and the reaction mixture was stirred at 0° C. for 45 mins. A fine precipitate began to form after about 30 mins. 5.33 L of cold acetone was added dropwise over 1.5 hr, and the suspension was allowed to stand for 15 mins, then filtered. The collected solid was washed with 5×500 mL (i.e., 2.50 L) of cold acetone, dried by suction under a high flow of nitrogen for 1.5 hr and dried in vacuo (room temperature/0.5 mm high vacuum) for 4 hr to give 139.1 g of the named product as an off-white solid (99.4% pure by HPLC analysis).

EXAMPLE 2

Preparation of
[6R-[6alpha,7beta(Z)]]-3-[[[6,8-Difluoro-1-(fluoro ethyl)-1,4-dihydro-7-(4-methyl-1-piperazinyl )-4-oxo-3-quinolinyl]carbonyl]oxy]methyl]-7-[[(methoxyimino)[2-[(triphenylmethyl)amino]-4-thiazolyl]acetyl]amino]-8-oxo-5-thia-1-azabicyclo[4,2,0]oct-2-ene-2-carboxylic acid The activated ester of formula

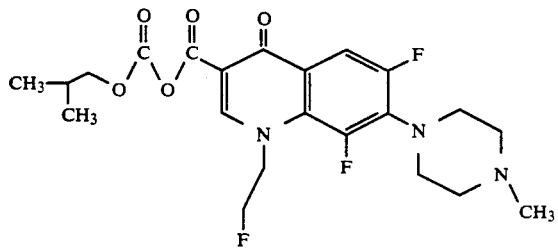

was prepared in situ from fleroxacin (738 mg, 2 mmol), isobutyl chloroformate (272 ul, 2.1 mmol), and tributylamine (714 ul, 3 mmol) in 16 ml of CH$_2$Cl$_2$. This clear solution was cooled to −50° C. Then a solution of 6R-[6alpha,7beta(Z)]]-3-(Hydroxymethyl)-7-[[(methoxyimino)[2(triphenylmethyl)amino]-4-thiazolyl]acetyl]amino]-B-oxo-5-thia-1-azabicyclo[4.2.0]oct-2-ene-2-carboxylic acid (1:1) tributylamine salt (1.344 g, 1.6 mmol) in 3 ml of CH$_2$Cl$_2$ was added followed by the addition of 4-dimethylaminopyridine (DMAP) (61 mg, 0.5 mmol) in 1 ml of CH$_2$Cl$_2$. The mixture was stirred at −20° C. for 3 hrs and then warmed to room temperature (i.e. about 25° C.) over 30 min. The reaction mixture was filtered through a 10–15 mesh glass filter in order to recover the unreacted fleroxacin (237 mg). To the filtrate, 25 ml of EtOAc followed by 25 ml of hexane were added.

The crude precipitate was collected (1.05 g). This crude product was dissolved in CH$_2$Cl$_2$ and 690 mg (43% yield) of the pure named compound was precipitated by the addition of acetone.

In an analogous manner [6R-[6alpha,7beta(Z)]]-3 -[[[[6,8-Difluoro-1-(2-fluoroethyl)-1,4-dihydro-7-(4-methyl-1-piperazinyl)-4-oxo-3-quinolinyl]carbonyl]oxy]methyl]-7[[(methoxyimino)[2-[(triphenylmethyl)amino]-4-thiazolyl]acetyl]amino]-8-oxo-5-thia-1-azabicyclo[4.2.0]oct-2-ene-2carboxylic acid was prepared using the following in place of the isobutyl chloroformate:

benzyl chloroformate,
menthyl chloroformate,
isopropenyl chloroformate,
trimethylacetyl chloride, and
1-methyl-2-fluoropyridinium p-toluenesulfonate, to activate the fleroxacin.

The results are summarized in Table I where the activating agent is represented by X.

TABLE I

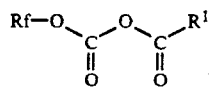

| X | Ester:Lactone | Yield % |
|---|---|---|
| —OH | —:— | No reaction |
| trimethylacetoxy- | 1:2 | ~10%* |
| F—** | 4:1 | 19% |
| isobutyloxycarbonyloxy- | 4:1 | 43% |
| benzyloxycarbonyloxy- | 4:1 | 30%* |
| cyclohexyloxy-carbonyloxy- | 4:1 | 56% |
| 2-menthyl-oxy-carbonyloxy- | 4:1 | 53% |
| 2-propenyloxy-carbonyloxy- | 2:1 | 30%* |

*Based on NMR analysis of crude product.
**Prepared in situ using 1-methyl-2-fluoropyridinium p-toluene-sulfonate The selection of other haloformates other than those specifically exemplified herein to activate the quinolone compound will be within the ability of persons skilled in the art in view of the present disclosure. Additionally, while there have been shown and described and pointed out fundamental novel features of the invention as applied to preferred embodiments thereof, it will be understood that various omissions and substitutions and changes in the form and details of the process and intermediates illustrated may be made by those skilled in the art without departing from the spirit of the invention. It is the intention, therefore, to be limited only as indicated by the scope of the claims appended hereto.

What is claimed is:

1. A compound of the formula

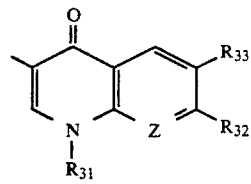

wherein $R^1$ is a group of the formula

wherein Z is $$\underset{\underset{\text{—C—}}{|}}{\overset{R_{30}}{}}$$

or N, $R_{30}$ is hydrogen or halogen; $R_{31}$ is hydrogen, halogen, lower alkyl, lower alkenyl, $C_3$-$C_7$ cycloalkyl, halo lower alkyl or mono, di and tri-halophenyl; $R_{30}$ and $R_{31}$ when taken together represent lower alkylene of 3-5 carbon atoms, a lower alkylene mono-oxy group of 2-4 carbon atoms or a lower alkylene dioxy group having 1-2 carbon atoms; $R_{32}$ is hydrogen, halogen, lower alkyl, a 5 or 6 membered heterocyclic ring containing 1-3 hetero atoms selected from the group consisting of O, N and S, the heterocyclic ring being unsubstituted or substituted with lower alkyl, lower alkoxy, halogen, halo substituted lower alkyl, amino lower alkyl, lower alkyl amino lower alkyl, amino, mercapto, hydroxy, carbamoyl or carboxy; $R_{33}$ is hydrogen or halogen; $R_{32}$ and $R_{33}$ when taken together represent a $C_1$-$C_4$ lower alkylene dioxy group; and $R_f$ is (i) alkyl or alkenyl, either of which may be unsubstituted or substituted with at least one halo, amino or cyano, (ii) aryl which may be unsubstituted or substituted with at least one halo, hydroxy, lower alkyl, amino, cyano, lower alkoxy or alkoxycarbonyl, (iii) aralkyl, or (iv) cycloalkyl which may be unsubstituted or substituted with at least one lower alkyl or lower alkenyl group.

2. The compound of claim 1, wherein Z is $$\underset{\underset{\text{—C—}}{|}}{\overset{R_{30}}{}}$$

$R_{30}$ is hydrogen, chlorine or fluorine $R_{31}$ is lower alkyl, halogen substituted lower alkyl, halogen, lower alkyl or $C_3$-$C_7$- cycloalkyl; $R_{32}$ is lower alkyl or piperazinyl which may be substituted on the 4-nitrogen atom with a lower alkyl group; and $R_{33}$ is hydrogen, chlorine or fluorine.

3. The compound of claim 2, wherein $R_{30}$ is hydrogen or fluorine $R_{31}$ is ethyl, fluoroethyl or cyclopropyl $R_{32}$ is methyl or piperazinyl which may be substituted on the 4-nitrogen atom with methyl; and $R_{33}$ is hydrogen or fluorine.

4. The compound of claim 3, wherein $R_{33}$ is fluorine.

5. The compound of claim 4, wherein $R^1$ has the formula

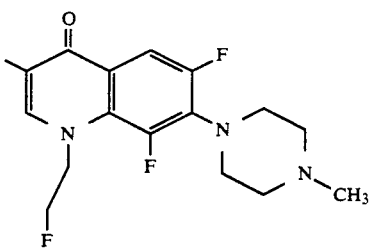

6. The compound of claim 5, wherein $R_f$ is alkyl, alkenyl or cycloalkyl, any of which may be unsubstituted or substituted as defined in claim 1.

7. The compound of claim 6, wherein $R_f$ is cyclohexyl.

* * * * *